United States Patent
Chen et al.

(10) Patent No.: US 6,524,620 B2
(45) Date of Patent: *Feb. 25, 2003

(54) DILTIAZEM CONTROLLED RELEASE FORMULATION AND METHOD OF MANUFACTURE

(75) Inventors: Chih-Ming Chen, Davie, FL (US); Xiu Xiu Cheng, Davie, FL (US); Steve Jan, Coral Springs, FL (US)

(73) Assignee: ANDRX Pharmaceuticals, Inc., Davie, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,323

(22) Filed: Jul. 20, 1998

(65) Prior Publication Data

US 2001/0007681 A1 Jul. 12, 2001

(51) Int. Cl.[7] ............................. A61K 9/52; A61K 9/54; A61K 31/554
(52) U.S. Cl. ....................... 424/490; 424/493; 424/494; 424/497; 514/211.06; 514/777; 514/786; 514/970
(58) Field of Search ................................. 424/494, 490, 424/528, 493, 497; 514/211.07, 777, 785, 786, 970

(56) References Cited

U.S. PATENT DOCUMENTS

| | | |
|---|---|---|
| 4,327,725 A | 5/1982 | Cortese et al. |
| 4,369,172 A | 1/1983 | Schor et al. |
| 4,555,398 A | 11/1985 | Oda |
| 4,612,008 A | 9/1986 | Wong et al. |
| 4,721,619 A | 1/1988 | Panoz et al. |
| 4,747,845 A | 5/1988 | Korol |
| 4,783,337 A | 11/1988 | Wong et al. |
| 4,792,452 A | 12/1988 | Howard et al. |
| 4,808,413 A | 2/1989 | Joshi et al. |
| 4,834,965 A | 5/1989 | Martani et al. |
| 4,839,177 A | 6/1989 | Colombo et al. |
| 4,859,470 A | 8/1989 | Guittard et al. |
| 4,869,904 A | 9/1989 | Uekama et al. |
| 4,880,631 A | 11/1989 | Haslam et al. |
| 4,886,668 A | 12/1989 | Haslam et al. |
| 4,891,230 A | 1/1990 | Geoghegan et al. |
| 4,894,240 A | 1/1990 | Geoghegan et al. |
| 4,898,737 A | 2/1990 | Panoz et al. |
| 4,917,899 A | 4/1990 | Geoghegan et al. |
| 4,925,837 A | 5/1990 | Cavero et al. |
| 4,952,402 A | 8/1990 | Sparks et al. |
| 4,960,596 A * | 10/1990 | Debregeas et al. ......... 424/458 |
| 4,963,365 A | 10/1990 | Samejima et al. |
| 4,966,769 A | 10/1990 | Guittard et al. |
| 4,983,401 A | 1/1991 | Eichel et al. |
| 4,992,277 A | 2/1991 | Sangekar et al. |
| 5,000,962 A | 3/1991 | Sangekar et al. |
| 5,002,776 A | 3/1991 | Geoghegan et al. |
| 5,008,114 A | 4/1991 | Lovrecich |
| 5,026,559 A | 6/1991 | Eichel et al. |
| 5,112,621 A | 5/1992 | Stevens et al. |
| 5,133,974 A | 7/1992 | Paradissis et al. |
| 5,137,733 A | 8/1992 | Noda et al. |
| 5,149,542 A | 9/1992 | Valducci |
| 5,156,850 A | 10/1992 | Wong et al. |
| 5,160,744 A | 11/1992 | Jao et al. |
| 5,169,638 A | 12/1992 | Dennis et al. |
| 5,169,865 A | 12/1992 | Ananthanarayanan et al. |
| 5,178,867 A | 1/1993 | Guittard et al. |
| 5,190,765 A | 3/1993 | Jao et al. |
| 5,208,037 A | 5/1993 | Wright et al. |
| 5,219,621 A | 6/1993 | Geoghegan et al. |
| 5,229,135 A * | 7/1993 | Philippon et al. ............ 424/494 |
| 5,232,705 A | 8/1993 | Wong et al. |
| 5,238,686 A | 8/1993 | Eichel et al. |
| 5,252,337 A | 10/1993 | Powell |
| 5,252,338 A | 10/1993 | Jao et al. |
| 5,260,068 A | 11/1993 | Chen |
| 5,286,497 A * | 2/1994 | Hendrickson et al. ....... 424/490 |
| 5,288,505 A | 2/1994 | Deboeck et al. |
| 5,324,280 A | 6/1994 | Wong et al. |
| 5,326,571 A | 7/1994 | Wright et al. |
| 5,336,504 A | 8/1994 | Geoghegan et al. |
| 5,344,657 A | 9/1994 | Desmolin |
| 5,354,556 A | 10/1994 | Sparks et al. |
| 5,354,560 A | 10/1994 | Lovrecich |
| 5,356,467 A | 10/1994 | Oshlack et al. |
| 5,364,620 A | 11/1994 | Geoghegan et al. |
| 5,376,384 A | 12/1994 | Eichel et al. |
| 5,391,377 A | 2/1995 | Barnwell |
| 5,419,917 A | 5/1995 | Chen et al. |
| 5,422,123 A | 6/1995 | Conte et al. |
| 5,439,689 A | 8/1995 | Hendrickson et al. |
| 5,445,829 A | 8/1995 | Paradissis et al. |
| 5,449,521 A | 9/1995 | Lovrecich |
| 5,458,888 A | 10/1995 | Chen |
| 5,464,633 A | 11/1995 | Conte et al. |
| 5,470,584 A | 11/1995 | Hendrickson et al. |
| 5,508,044 A | 4/1996 | Buxton et al. |
| 5,518,730 A | 5/1996 | Fuisz |
| 5,529,790 A * | 6/1996 | Eichel et al. ................ 424/480 |
| 5,529,791 A * | 6/1996 | Deboeck et al. ............. 424/494 |
| 5,567,441 A * | 10/1996 | Chen .......................... 424/494 |
| 5,578,321 A | 11/1996 | Sherman |
| 5,601,845 A | 2/1997 | Buxton et al. |

(List continued on next page.)

Primary Examiner—Christopher S. F. Low
Assistant Examiner—Anish Gupta
(74) Attorney, Agent, or Firm—Hedman & Costigan, P.C.

(57) ABSTRACT

A controlled release diltiazem dosage formulation comprising a plurality of active pellets coated with an extended release coating wherein the active pellets contain diltiazem or a pharmaceutically acceptable salt, a pharmaceutically acceptable inert seed and a binder and the extended release coating contains a water insoluble water permeable polymer, a channeling agent, a lubricant and optionally a surfactant. A single batch intermittent method of manufacturing a heterogeneous population of extended release pellets for use as a dosage formulation is also disclosed.

26 Claims, 8 Drawing Sheets

U.S. PATENT DOCUMENTS

| | | |
|---|---|---|
| 5,616,345 A | 4/1997 | Geoghegan et al. |
| 5,616,593 A | 4/1997 | Patel et al. |
| 5,622,716 A | 4/1997 | Barth et al. |
| 5,629,022 A | 5/1997 | Perovitch et al. |
| 5,637,309 A | 6/1997 | Tajima et al. |
| 5,670,172 A | 9/1997 | Buxton et al. |
| 5,681,583 A | 10/1997 | Conte et al. |
| 5,683,721 A | 11/1997 | Perovitch et al. |
| 5,700,410 A | 12/1997 | Nakamichi et al. |
| 5,709,885 A | 1/1998 | Hellen et al. |
| 5,738,874 A | 4/1998 | Conte et al. |
| 5,741,822 A | 4/1998 | Yesair |
| 5,834,024 A | * 11/1998 | Heinicke et al. ............ 424/497 |

\* cited by examiner

US 6,524,620 B2

DILTIAZEM CONTROLLED RELEASE FORMULATION AND METHOD OF MANUFACTURE

BACKGROUND OF THE INVENTION

The present invention relates to a controlled release formulation for the drug diltiazem or its pharmaceutically acceptable salts thereof and a method for manufacturing a controlled release dosage formulation containing diltiazem or a pharmaceutically acceptable salt thereof as the active ingredient.

Diltiazem hydrochloride, commonly referred to as diltiazem, is a benzothiazine derivative that blocks the influx of calcium ions in smooth and cardiac muscle and has few side effects. Diltiazem has been shown to be useful in alleviating symptoms of chronic heart disease, particularly angina pectoris, myocardial ischemia and hypertension. Diltiazem also has been shown to have activity against arrythmia and may be useful in treating congestive cardiac insufficiency, Raynaud's syndrome and peripheral and cerebral circulatory insufficiency.

Diltiazem is sold commercially in extended release pharmaceutical dosage forms that attempt to maintain a therapeutic serum level of diltiazem and minimize the effects of missed doses of the drug caused by lack of patient compliance. One commercial form of extended release diltiazem is Cardizem CD®. Cardizem CD® is described as a once-a-day extended release capsule containing diltiazem HCl and fumaric acid. In the prosecution history of U.S. Pat. No. 5,286,497, representations were made that the formulation disclosed in that patent is the formulation for Cardizem CD®. The formulation for Cardizem CD® is identified in the prosecution history of U.S. Pat. No. 5,286,497 as having a "stair step release profile" that is created by a blend of two types of beads referred to as a rapid release bead and an extended release bead.

Another commercially available extended release form of diltiazem HCl is marketed under the trademark Dilacor XR®. This formulation is described as a once-a-day capsule which contains multiple units of diltiazem HCl. The Dilacor XR® product is described in U.S. Pat. No. 4,839,177 which teaches that the tablets or multiple units which are placed in the capsule comprise a core of diltiazem HCl and a swellable polymer and a support platform applied to the tablet.

A third commercially available form of extended release diltiazem HCl is sold under the tradename Tiazac™ or Viazem™. U.S. Pat. No. 5,529,791 is listed with the United States Food and Drug Administration as relating to the Tiazac™ product. U.S. Pat. No. 5,529,791 discloses an extended release form of diltiazem containing beads that comprise diltiazem HCl and a wetting agent. The beads are coated with a microporous membrane comprising a water soluble or water dispersible polymer and a water, acid and basic insoluble polymer.

Numerous other controlled release diltiazem formulations are in the prior art such as: U.S. Pat. No. 5,229,135 which discloses a once-a-day formulation containing a single pellet that is prepared with an active core coated with diltiazem and an inner and outer membrane surrounding the core; U.S. Pat. No. 4,960,596 which discloses a slow release preparation of diltiazem containing microgranules that comprise neutral excipients and diltiazem wherein the microgranules are coated with shellac and ethylcellulose; and Patent Cooperation Treaty Application No. WO 96/17598 which discloses a diltiazem formulation that is described as being suitable for once daily administration and contains three types of beads that release diltiazem at different time periods. Other diltiazem formulations are disclosed in U.S. Pat. Nos.: 4,721,619; 4,894,240; 5,002,776; 5,364,620; 4,891,230; 4,917,899; 5,288,505; 5,336,504; 5,470,584; 5,439,689; 5,376,384; 5,529,790; and 5,567,441.

It is an object of the present invention to provide a novel once-a-day diltiazem formulation that does not employ a mixture of the diltiazem and an organic acid or a wetting agent in the core.

It is also an object of the present invention to provide a novel process for manufacturing a once-a-day diltiazem formulation.

SUMMARY OF THE INVENTION

The foregoing objectives are meet by the present invention that is directed to a controlled release pharmaceutical dosage formulation comprising a plurality of active pellets coated with an extended release coating to form extended release pellets.

The active pellets comprises:
  (i) 10–30% of a pharmaceutically acceptable inert seed;
  (ii) 50–85% of diltiazem; and
  (iii) 1–15% of a binder.
All the foregoing percentages are based upon the total weight of the active pellets.

The extended release coating comprises:
  (i) 60–85% of a water insoluble water permeable polymer;
  (ii) 0.5–5% of a water or acid soluble channeling agent;
  (iii) 10–40% of a lubricant; and
  (iv) optionally less than 1% of a surfactant.
All the foregoing percentages are based upon the total weight of the extended release coating.

The extended release coating can be applied to the active pellets by any means commonly used in the industry such as pan coating or air suspension techniques. It is preferred that the extended release coating be applied to the active pellets in a fluidized bed coater, preferably a Wurster type coater.

The controlled release pharmaceutical dosage formulation of the present invention can be administered to a patient in a free dosage form such as mixing a predetermined amount of the extended release pellets into food for administration or in a unit dosage form such as a gelatin capsule or tablet that contains a plurality of the extended release pellets.

The dosage formulation of the present invention may contain a homogeneous population of extended release pellets wherein each pellet comprises approximately the same amount or thickness of extended release coating. The dosage form of the present invention may also contain a heterogeneous population of extended release pellets wherein the population comprises a blend or mixture of pellets with different amounts or thicknesses of extended release coating.

A heterogeneous population of extended release pellets of the present invention can be obtained in a single batch intermittent coating process and thereby eliminate the need for several separate coating batches and a separate and distinct blending step. The unique process comprises adding a first allotment of active pellets to a coating equipment; coating the first allotment of active pellets with a first amount of extended release coating; adding a second allotment of active pellets to the coating equipment after the coating of the first allotment of active pellets with the first amount of extended release coating and coating the first and second allotment of active pellets with a second amount of extended release coating. Additional allotments, i.e. a third allotment or a fourth allotment, of active pellets may also be added to the coating equipment at subsequent time periods during the coating process and coating all the allotments of active pellets with additional amounts of extended release coating. Once the coating process is completed a heterogeneous population of pellets is obtained wherein the first allotment of active pellets has the greatest amount of or thickest extended release coating, the second allotment of active pellets are coated with less extended release coating than the first allotment, and the third allotment of active pellets, if employed, are coated with less extended release coating than the first and second allotments of active pellets.

The heterogeneous population of pellets prepared in accordance with the single batch intermittent process of the present invention has the advantage of eliminating the blending or mixing steps required to produce the bead blends of the prior art such as the Cardizem CD® product. The heterogeneous population also has the advantage of producing a population of pellets that provides a constant therapeutic amount of the diltiazem over a twenty-four hour period because each allotment of pellets will release the diltiazem at a different time period.

DETAILED DESCRIPTION OF THE INVENTION

Figure 1:
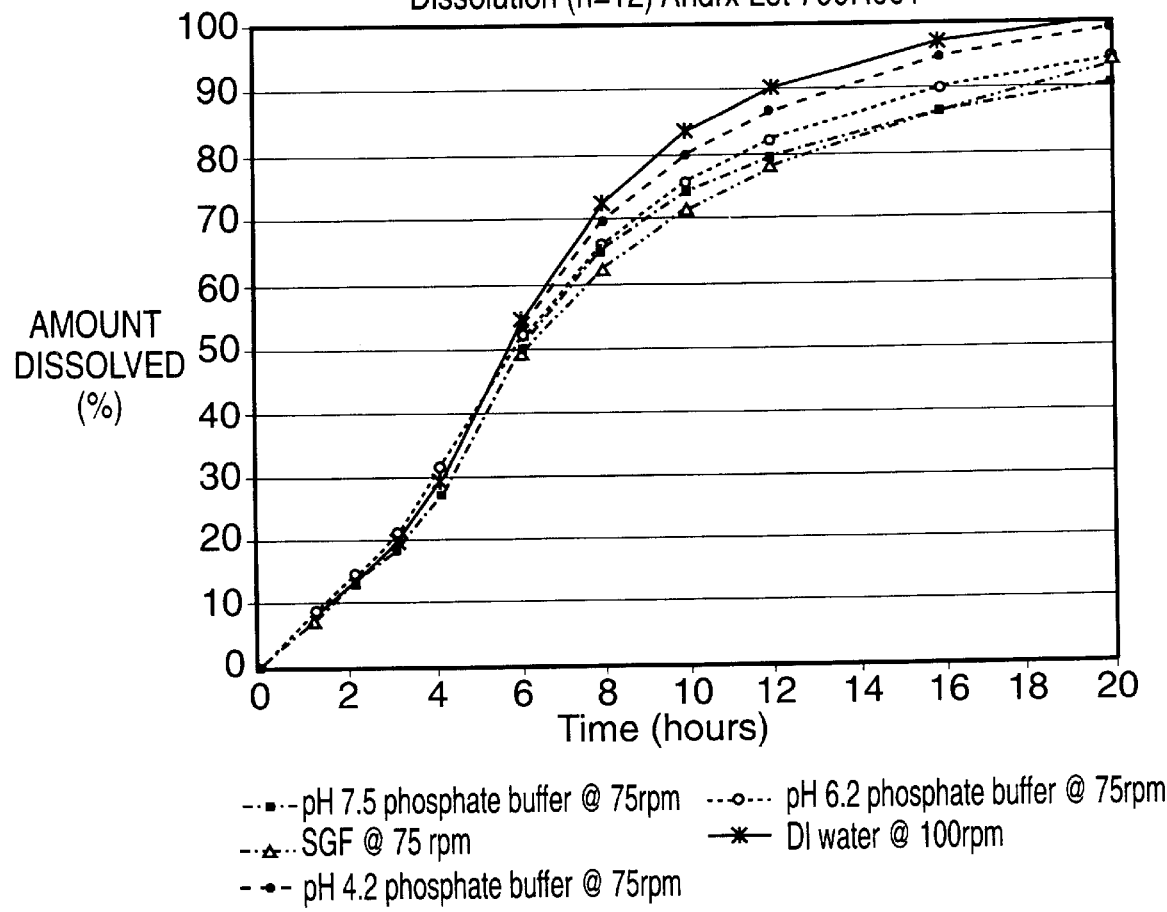
FIG. 1 is a graph depicting the dissolution profile in simulated intestinal fluid (pH 7.5 phosphate buffer), simulated gastric fluid (SGF), pH 4.2 phosphate buffer, pH 6.2 phosphate buffer, and deionized water of the formulation described in Example 1 as tested according to the procedure described in United States Pharmacopeia XXIII, Apparatus 2 @ 75 rpm unless otherwise noted.
Figure 2:
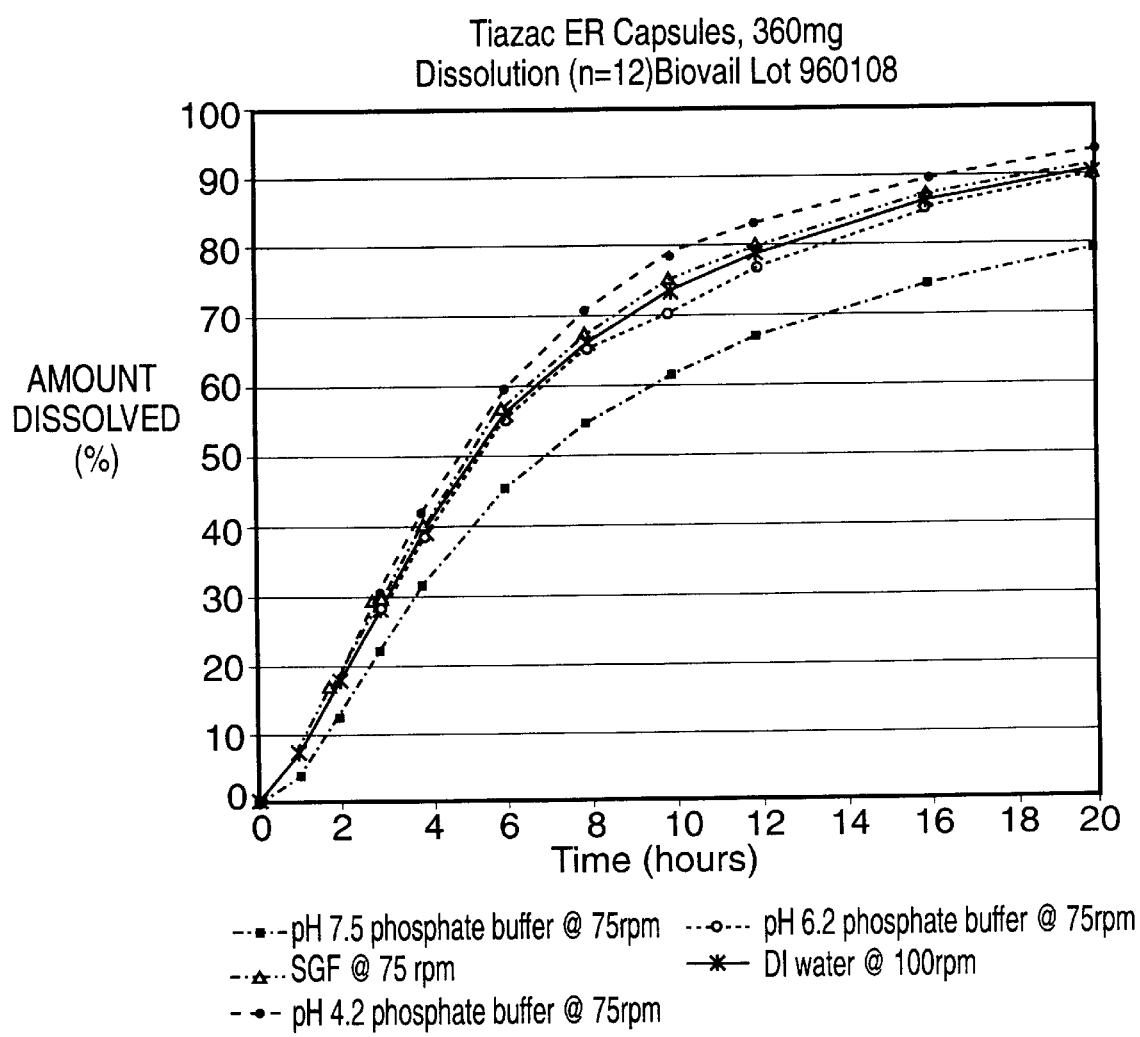
FIG. 2 is a graph depicting the dissolution profile in simulated intestinal fluid (pH 7.5 phosphate buffer), simulated gastric fluid (SGF), pH 4.2 phosphate buffer, pH 6.2 phosphate buffer, and deionized water of TIAZAC™, a commercially available dosage form of diltiazem, as tested according to the procedure described in United States Pharmacopeia XXIII, Apparatus 2 @ 75 rpm unless otherwise noted.

The diltiazem or a pharmaceutically acceptable salt thereof used in the present invention should be micronized and preferably have a particle size of less than 20 microns.

The pharmaceutically acceptable inert seed can be any type of commonly known starting material such as a starch or sugar sphere having a diameter ranging from about 15–50 mesh and more preferably about 30–35 mesh.

The binder employed in the active pellets can be any type of binding agent commonly known in the art such as polyvinyl pyrrolidone, hydroxyethylcellulose, hydroxypropyl cellulose, hydroxypropyl methylcellulose, polyacrylate, ethylcellulose or mixtures of the foregoing. In the preferred embodiment of the present invention, the binder for the active pellets is a combination of a water soluble binder, such as polyvinyl pyrrolidone or hydroxyethylcellulose and a water insoluble binder such as ethylcellulose or a polyarcylate. The ratio of water soluble binder to water insoluble binder should be about 1:1 to about 1:3 with the most preferred ratio being 1:2. These ratios are based upon the weight of the water soluble binder to the weight of the water insoluble binder in the active pellets.

The active pellets of the present invention will comprise the following ingredients:

| INGREDIENT | PREFERRED | MOST PREFERRED |
| --- | --- | --- |
| diltiazem HCl | 50–85% | 65–80% |
| inert seed | 10–30% | 15–25% |
| binder | 1–15% | 4–10% |

In a preferred embodiment of the present invention the active pellets will comprise the following ingredients:

| INGREDIENT | PREFERRED | MOST PREFERRED |
| --- | --- | --- |
| diltiazem HCl | 50–85% | 65–80% |
| inert seed | 10–30% | 15–25% |
| water soluble binder | 0.25–5% | 1–3.4% |
| water insoluble binder | 0.75–10% | 3–6.6% |

All the percentages in the above tables are based on the total weight of the active pellets.

The active pellets of the present invention which comprise the diltiazem HCl is prepared by forming a suspension of the binder and drug, and then layering the suspension onto the inert seed using any of the layering techniques commonly known in the industry such as fluidized bed coating, rotor granulation or pan coating.

The extended release coating that is applied to the active pellets to control the release of the drug from the dosage form comprises a water insoluble water permeable polymer, a water or acid soluble channeling agent, a lubricating or dusting agent and optionally a surfactant.

Suitable water insoluble water permeable polymers are ethylcellulose, cellulose acetate and polyacrylates or mixtures thereof. In the preferred embodiment of the present invention, the water insoluble water permeable polymer is a polymethacrylate ester copolymer, such as a poly (ethylarcylate methylmethacrylate) copolymer which is commercially available from Rohm Pharma under the tradename EUDRAGIT NE 30D.

The channeling agent employed in the extended release coating can be any type of water or acid soluble pharmaceutically acceptable substance commonly known in the art such as polyvinyl pyrrolidone, hydroxyethylcellulose, hydroxypropyl cellulose, hydroxypropyl methylcellulose, polyacrylate, sucrose, drug itself or any combination of the foregoing. The preferred channeling agent is a water or acid soluble polymer such as hydroxypropyl methylcellulose.

Suitable lubricants or dusting agents that can be used in the present invention are talc, magnesium stearate, silicon dioxide, kaolin or a mixture of the foregoing. The lubricant or dusting agent prevents the pellets from sticking to one another during processing. The lubricant may be dusted onto the active pellets during the coating process or it may be incorporated into a coating suspension and applied to the core with the coating suspension. In a preferred embodiment of the present invention, the lubricant is a mixture of talc and magnesium stearate. The preferred ratio of talc to magnesium stearate should be about 1:2 to about 2:1. These ratios are based upon the weight of the talc to the weight of the magnesium stearate.

Suitable surfactants that may optionally be used in the present invention are sodium lauryl sulfate, sodium taurocholate or a polysorbate. The preferred surfactant is polysorbate 80.

The extended release coating can be applied to the active pellets by any means commonly known in the industry such as a rotary granulator, pan coater or a fluidized bed coater.

The extended release coating of the present invention will have the following composition:

| COATING: | Preferred | Most Preferred |
| --- | --- | --- |
| water insoluble polymer | 60–85% | 65–80% |
| channeling agent | 0.5–5% | 0.75–2% |
| lubricant | 10–40% | 15–30% |
| surfactant (optionally) | less than 1% | less than 0.5% |

In a preferred embodiment of the present invention the extended release coating will comprise the following ingredients:

| COATING: | Preferred | Most Preferred |
| --- | --- | --- |
| water insoluble polymer | 60–85% | 65–80% |
| channeling agent | 0.5–5% | 0.75–2% |
| talc | 5–20% | 7.5–15% |
| magnesium stearate | 5–20% | 7.5–15% |
| surfactant (optionally) | less than 1% | less than 0.5% |

The percentages listed in the above tables are based on the total weight of the extended release coating.

Generally, the extended release coating will comprise from about 1% to about 20%, preferably about 1.5% to about 15%, based on the total weight of the active pellet and extended release coating.

The dosage form of the present invention may be a homogeneous population of extended release pellets wherein all the pellets in the dosage form have approximately the same amount or thickness of extended release coating applied to all the active pellets.

The dosage form of the present invention may also be a heterogeneous population of pellets wherein the dosage form comprises pellets with varying amounts or thicknesses of extended release coating applied to the active pellets. For example the heterogeneous population may comprise a mixture of homogeneous pellets as defined above and uncoated active pellets that provide an immediate release amount of the diltiazem. The heterogeneous population may also be formed by blending extended release pellets that are prepared with different amounts or thicknesses of extended release coating. The extended release pellets with varying thicknesses may be prepared in separate and distinct batches or by the single batch intermittent process of the present invention wherein multiple allotments of active pellets are added to a coating equipment at periodic time intervals during the coating process.

In a preferred embodiment of the present invention a heterogeneous population of extended release pellets are prepared in a single batch intermittent process using fluidized bed coating equipment wherein the population is prepared by adding three separate allotments of active pellets to the coating equipment during the coating process. The process comprises the steps of:

1) adding a first allotment of active pellets to the coating equipment;
2) coating the first allotment of active pellets with a first amount of extended release coating;
3) adding a second allotment of active pellets to the coating equipment;
4) coating the first and second allotment of active pellets with a second amount of extended release coating;
5) adding a third allotment of active pellets to the coating equipment; and
6) coating the first, second and third allotments of active pellets with a third amount of extended release coating.

Suitable once-a-day dosage formulations can be prepared wherein the amounts of the first, second and third allotments of active pellets added to the coating equipment are equal, however it is preferred that the active pellets be added to the coating equipment in the following proportions:

| Allotment | Preferred % | Most Preferred % |
| --- | --- | --- |
| first | 34–90% | 65–85% |
| second | 5–33% | 5–15% |
| third | 5–43% | 15–25% |

All the percentages in the above table are based on the total weight of the active pellets in the dosage formulation.

Suitable once-a-day dosage formulations can also be prepared according to the above described process wherein the quantity of the first, second and third amounts of extended release coating are equal, however, it is preferred that the quantities of the first, second and third amounts of extended release coating be as follows:

| Coating | Preferred % | Most Preferred % |
| --- | --- | --- |
| first | 10–33% | 15–25% |
| second | 34–80% | 50–75% |
| third | 10–40% | 15–30% |

All the percentages in the above table are based on the total weight of the extended release coating to be applied to the active pellets in the dosage formulation.

In the most preferred embodiment of the present invention, the extended release coating is applied to the active pellets with an atomization pressure of 2–5 bars, product temperature of 20–30° C., and a spray rate of: 100–600 g/min for the first amount of extended release coating; 200–1100 g/min for the second amount of extended release coating and 500–1100 g/min for the third amount of the extended release coating.

The dosage formulation prepared according to the present invention should exhibit the following dissolution profile when tested in a USP type 2 apparatus at 75 rpms in 900 ml of simulated intestinal fluid (pH 7.5 phosphate buffer) and at 37° C.:

| Time (hours) | Preferred | Most Preferred |
| --- | --- | --- |
| 2 | 0–30% | 5–25% |
| 4 | 10–50% | 15–45% |
| 8 | 30–85% | 45–80% |
| 12 | 45–90% | 60–85% |
| 16 | NLT 60% | NLT 70% |
| 20 | NLT 70% | NLT 75% |

NLT = NOT LESS THAN

The controlled release dosage formulations prepared according to the present invention should exhibit the following dissolution profile when tested in a USP type 2 apparatus at 75 rpms in 900 ml of simulated gastric fluid (SGF) and at 37° C.:

| Time (hours) | Preferred | Most Preferred |
| --- | --- | --- |
| 2 | 0–30% | 5–25% |
| 4 | 10–50% | 15–45% |
| 8 | 25–80% | 40–75% |
| 12 | 50–90% | 55–85% |
| 16 | NLT 55% | NLT 65% |
| 20 | NLT 65% | NLT 70% |

NLT = NOT LESS THAN

The controlled release dosage formulations prepared according to the present invention should exhibit the following dissolution profile when tested in a USP type 2 apparatus at 100 rpms in 900 ml of 0.1 N HCl and at 37° C.:

| Time (hours) | Preferred | Most Preferred |
| --- | --- | --- |
| 2 | 0–30% | 5–25% |
| 4 | 5–45% | 10–35% |
| 8 | 20–70% | 35–65% |
| 12 | NLT 45% | NLT 50% |
| 18 | NLT 55% | NLT 60% |
| 20 | NLT 65% | NLT 70% |

NLT = NOT LESS THAN

DESCRIPTION OF THE PREFERRED EMBODIMENTS

The following examples illustrate the present invention and are not intended to limit the scope of the present invention.

EXAMPLE 1

A dosage form containing a heterogeneous population of pellets in accordance with the present invention is prepared by forming active pellets having the following composition:

| I ACTIVE PELLET | |
| --- | --- |
| diltiazem HCl, USP (micronized)[1] | 75.0% |
| sugar sphere, NF[2] | 18.18% |
| ethylcellulose, NF (ETHOCEL 10 cps) | 4.56% |
| povidone, USP (K-30) | 2.27% |

[1]average particle size of less than 20 microns.
[2]30/35 mesh.

The active core is prepared by adding 10.94 kg of the ethylcellulose to 364.72 kg of isopropyl alcohol while mixing with a tri-blender and homogenizing for about 30 minutes. Once the ethylcellulose is dissolved, 5.45 kg of povidone is added to the ethylcellulose solution and homogenized for an additional 10 minutes. After the ethylcellulose and povidone are dissolved, 180 kg of diltiazem is added to the ethylcellulose/povidone solution while mixing until a uniform suspension is obtained. The diltiazem suspension is then applied to 43.63 kg of the sugar spheres in a fluidized bed coater under the following conditions: product temperature is 26–30° C.; atomization pressure is 2–4 bar; air volume of 700–1800 CFM and a pump rate of 300–1500 g/min.

Once the diltiazem suspension is consumed, the active pellets are dried in the fluidized bed coater for approximately 10 minutes or until the LOD (loss on drying) is less than 1%. Once the drying stage is completed, the dried diltiazem active pellets are sieved and placed in a clean, properly labeled double polyethylene bag lined container.

The active pellets sized between 14 and 25 mesh are coated with an extended release coating in a single batch intermittent coating process to form a heterogeneous population of pellets wherein the extended release coating has the following composition:

| II Extended Release Coating | |
| --- | --- |
| | Weight % |
| Eudragit NE 30D[1], EP | 73.66% |
| hydroxypropyl methylcellulose, USP (Methocel E5) | 1.00% |
| talc, USP(I) | 12.59% |
| magnesium stearate, NF | 12.59% |
| polysorbate 80, NF | 0.17% |

[1]30% aqueous dispersion

The controlled release coating is prepared by adding 0.120 kg of the Methocel E5 to 15.05 kg of purified water, USP, and mixing with a mechanical stirrer for approximately 60 minutes. 1.510 kg of talc is then added to the Methocel E5/water mixture while mixing.

In a separate container, 0.0204 kg of polysorbate 80 is added to 4.46 kg of isopropyl alcohol and mixed with a mechanical mixer for approximately 2 minutes. 1.510 kg of magnesium stearate is added to the polysorbate 80/isopropyl alcohol mixture and the mixing is continued for approximately 5 minutes.

Once the magnesium stearate has been mixed, the Methocel E5 and talc mixture is added to the magnesium stearate/polysorbate 80 mixture. The resulting composition is mixed for about 3 minutes.

After gently shaking, the Eudragit NE 30D is weighed and filtered through an 80 mesh stainless steel screen. The mixture of Methocel E5, talc, magnesium stearate, polysorbate 80 is added to the Eudragit NE 30D and mixed with a mechanical mixer for at least ten minutes before applying the resulting extended release coating suspension to the active pellets using a Wurster type fluidized bed coater. Stirring of the extended release coating should continue throughout the coating process.

The extended release coating suspension with the above composition is applied to the active pellets by adding 77.00 kg of a first allotment of active pellets to the Wurster type fluidized bed coater and preheating the first allotment of active pellets for two minutes with an inlet temperature 40° C. The extended release coating suspension is applied to the first allotment of active pellets under the following conditions: product temperature 23–27° C.; atomization pressure 3–4 bars; and a pump rate of 200–300 g/min. After approximately 8.70 kg of extended release coating suspension has been applied to the first allotment of active pellets, the coated active pellets are cooled in the coater until the air inlet temperature reaches approximately 25° C.

Once the first allotment of active pellets are cooled, approximately 10.00 kg of a second allotment of active pellets are added to the coater. The first and second allotment of active pellets are then coated with approximately 30.43 kg of extended release coating suspension under the following conditions: product temperature 23–27° C.; atomization pressure 3–4 bars; and a pump rate of 300–800 g/min. After the 30.43 kg of extended release coating suspension is applied to the first and second allotment of active pellets, the coated first and second allotment of active pellets are cooled in the coater until the air inlet temperature reaches approximately 25° C.

After the coated first and second allotment of active pellets are cooled, approximately 18.00 kg of a third allotment of active pellets are added to the coater. The first, second and third allotment of active pellets are then coated with remaining amount of the extended release coating suspension under the following conditions: product temperature 23–27° C.; atomization pressure 3–4 bars; and a pump rate of 600–800 g/min. After all the extended release coating suspension is consumed, the first, second and third coated allotments of active pellets are cooled and dried in the fluidized bed coater until the LOD is less than 1%. Thereafter the coated pellets are dusted with 2.34 kg of talc and dried in an oven for 40 hours at 60° C. and sieved using a sieve equipped with 12 mesh and 24 mesh screens.

The resulting heterogeneous population of extended release coated pellets are encapsulated into hard gelatin capsules in an amount to provide approximately 360 mg of diltiazem in each capsule and are tested in simulated intestinal fluid (pH 7.5 phosphate buffer), simulated gastric fluid (SGF), pH 6.2, pH 4.2, deionized water and 0.1 N HCl according to the procedure described in United States Pharmacopeia XXIII, using Apparatus 2 @ 75 rpm (unless otherwise noted) and the number of test vessels is 12 unless otherwise noted. The results of the in vitro tests are as follows:

| TIME (hours) | pH 7.5 % Released | SGF % Released | pH 4.2 % Released |
| --- | --- | --- | --- |
| 2 | 14 | 11 | 12 |
| 4 | 27 | 29 | 29 |
| 8 | 65 | 62 | 70 |
| 12 | 79 | 78 | 87 |
| 16 | 87 | 86 | 95 |
| 20 | 91 | 94 | 99 |

| TIME (hours) | pH 6.2 % Released | DI $H_2O$[1] % Released | 0.1 N HCl[1,2] % Released |
| --- | --- | --- | --- |
| 2 | 14 | 14 | 10 |
| 4 | 31 | 29 | 22 |
| 8 | 66 | 72 | 50 |
| 12 | 82 | 90 | 68 |
| 16 | 90 | 97 | 79 |
| 20 | 94 | 101 | 86 |

[1]test conducted at 100 rpm.
[2]only six (6) vessels tested.

Figure 3:
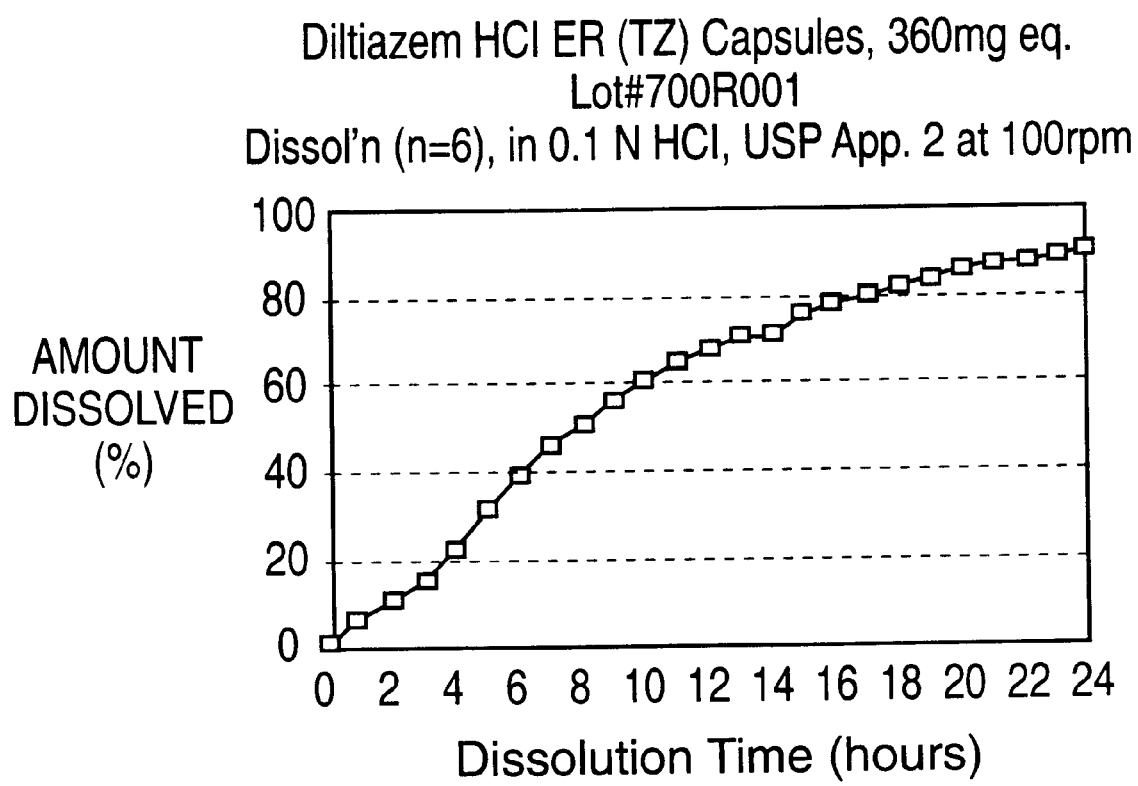
FIG. 3 is a graph depicting the dissolution profile in 0.1 N HCl of the formulation described in Example 1 as tested according to the procedure described in United States Pharmacopeia XXIII, Apparatus 2 @ 100 rpm.

The release profile in pH 7.5, SGF, pH 4.2, pH 6.2, deionized water and 0.1 N HCl of the controlled release dosage product prepared in this Example is shown in FIGS. 1 and 3.

Figure 5:
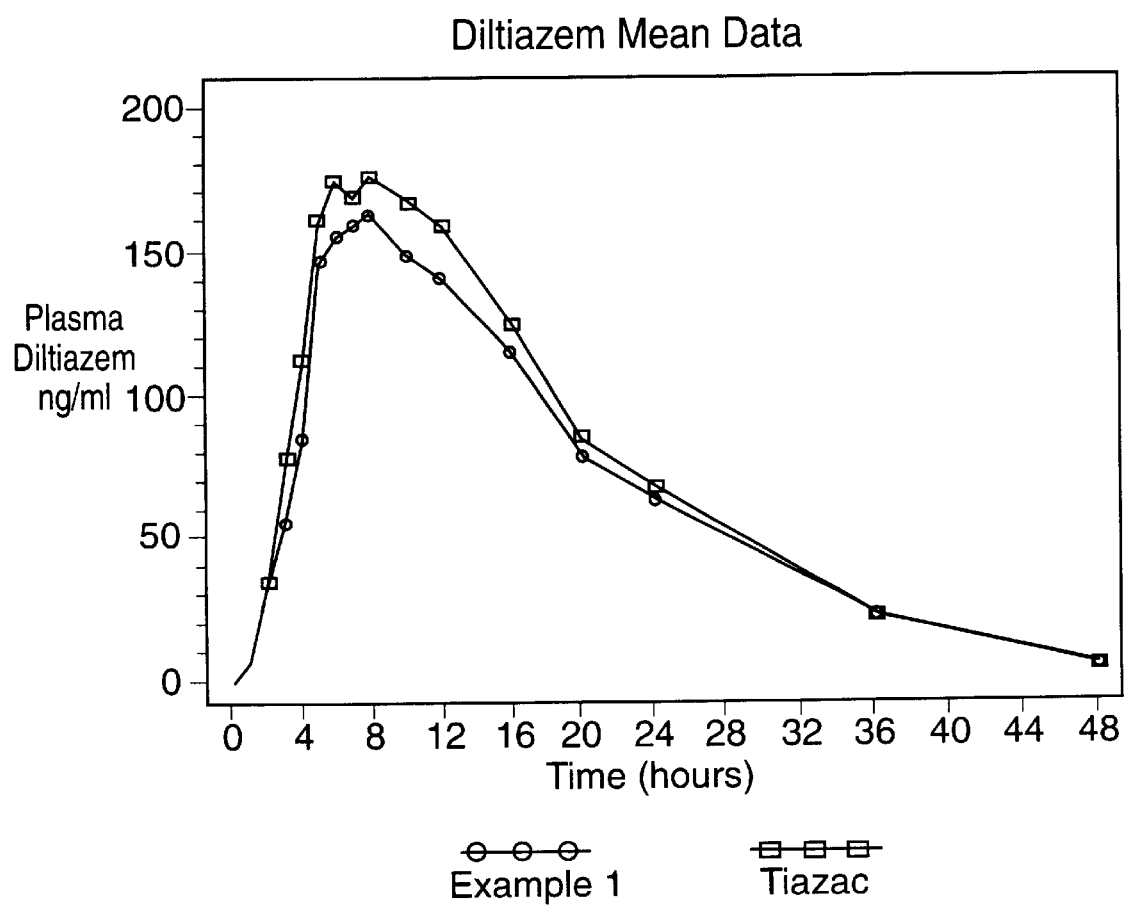
FIG. 5 is a graph depicting the linear plot of the mean plasma diltiazem concentration verses time of the formulation described in Example 1 and the linear plot of the mean plasma diltiazem concentration verses time of the commercially available diltiazem product TIAZAC™.

FIG. 5 depicts the in vivo diltiazem plasma profile of the controlled release product prepared in this Example. Also shown in FIG. 5 is the in vivo diltiazem plasma profile of TIAZAC™, a commercially available pharmaceutical product containing the drug diltiazem HCl that employs a mixture of diltiazem HCl and a wetting agent in the core.

Table 1 is a summary of the bioavailability comparison data under fasting conditions, test/reference ratio, shown in FIG. 5 wherein the TIAZAC™ product is the reference product in a two way crossover biostudy with n=30.

TABLE 1

|  | Test Mean | Ref Mean | Test/Ref Ratio |
| --- | --- | --- | --- |
| $C_{max}$(ng/ml) | 184.09 | 202.67 | 0.908 |
| $AUC_{inf}$(ng · hr/ml) | 3306.49 | 3568.75 | 0.927 |
| $T_{max}$(hr) | 7.97 | 7.93 | 1.005 |
|  | Test G. Mean | Ref. G. Mean | G Mean Ratio |
| $C_{max}$(ng/ml) | 171.81 | 184.70 | 0.930 |
| $AUC_{inf}$(ng · hr/ml) | 3089.14 | 3257.33 | 0.948 |

Figure 6:
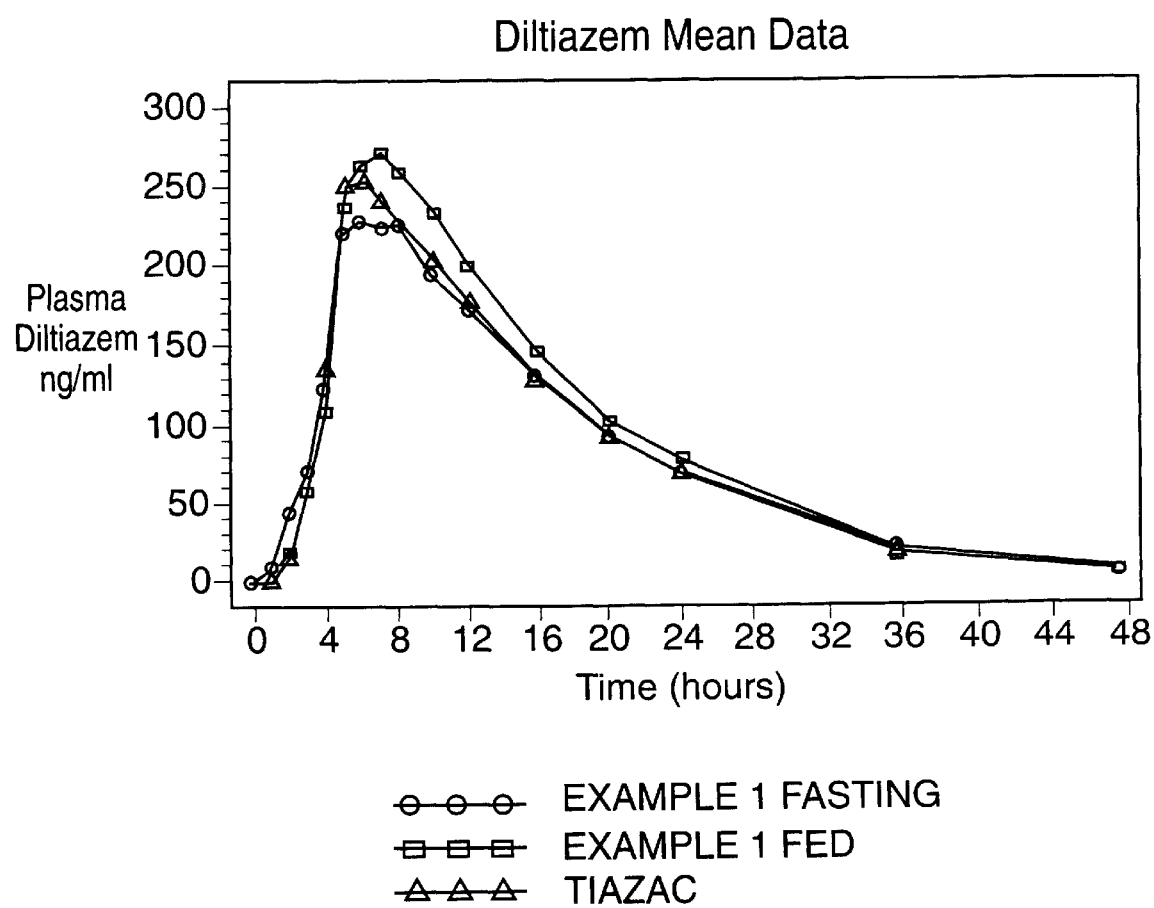
FIG. 6 is a graph depicting the linear plot of the mean plasma diltiazem concentration verses time of the formulation described in Example 1 under fed and fasting conditions and the linear plot of the mean plasma diltiazem concentration verses time of the commercially available diltiazem product TIAZAC™ under fed conditions.

FIG. 6 depicts the in vivo diltiazem plasma profile of the controlled release product prepared in this Example under fed and fasting conditions. FIG. 6 also shows the in vivo diltiazem plasma profile of the TIAZAC™ product under fed conditions.

Table 2 is a summary of the bioavailability comparison data under non-fasting conditions, test/reference ratio, shown in FIG. 6 wherein the TIAZAC™ product is the reference product in a three way crossover biostudy with n=23.

TABLE 2

|  | Test Mean | Ref Mean | Test/Ref Ratio |
| --- | --- | --- | --- |
| $C_{max}$(ng/ml) | 287.51 | 266.25 | 1.08 |
| $AUC_{inf}$(ng · hr/ml) | 4297.05 | 4038.74 | 1.06 |
| $T_{max}$(hr) | 6.69 | 5.79 | 1.16 |
|  | Test G. Mean | Ref. G. Mean | G Mean Ratio |
| $C_{max}$(ng/ml) | 271.60 | 256.05 | 1.06 |
| $AUC_{inf}$(ng · hr/ml) | 4035.33 | 3838.23 | 1.05 |

EXAMPLE 2

A dosage form containing a homogeneous population of pellets in accordance with the present invention is prepared by forming an active pellet as described in Example 1.

The active pellets are coated with an extended release coating in a one step coating process to form a homogeneous population of pellets wherein the extended release coating is prepared as described in Example 1 and has the following composition:

| II Extended Release Coating | |
|---|---|
| Eudragit NE 30D, EP | 73.82% |
| hydroxypropyl methylcellulose, USP (Methocel E5) | 0.96% |
| talc, USP(I) | 12.61% |
| magnesium stearate, NF | 12.61% |

347.83 g of extended release coating suspension with the above composition is applied to 602 g of active pellets in a fluidized bed coater under the following conditions: inlet air temperature of 25–35° C.; atomization pressure of 1.5–2.5 bars; and a pump rate of 3–10 ml/min.

The coated active pellets are cooled and dried in the fluidized bed coater until the LOD is less than 1%. Thereafter the coated pellets are dusted with 2.34 kg of talc and dried in an oven for 40 hours at 60° C. and sieved using a sieve equipped with 12 mesh and 24 mesh screens.

The resulting homogeneous population of extended release coated pellets are encapsulated into hard gelatin capsules so that approximately 360 mg of diltiazem are in each capsule. The capsules are tested in simulated intestinal fluid (SIF) and simulated gastric fluid (SGF) according to the procedure described in United States Pharmacopeia XXIII, using Apparatus 2 @ 75 rpm and found to have the following release profile:

| Time (hours) | SIF % Released | SGF % Released |
|---|---|---|
| 2 | 11 | 9 |
| 4 | 35 | 29 |
| 8 | 65 | 56 |
| 12 | 76 | 68 |
| 16 | 83 | 77 |
| 20 | 87 | 83 |

Figure 4:
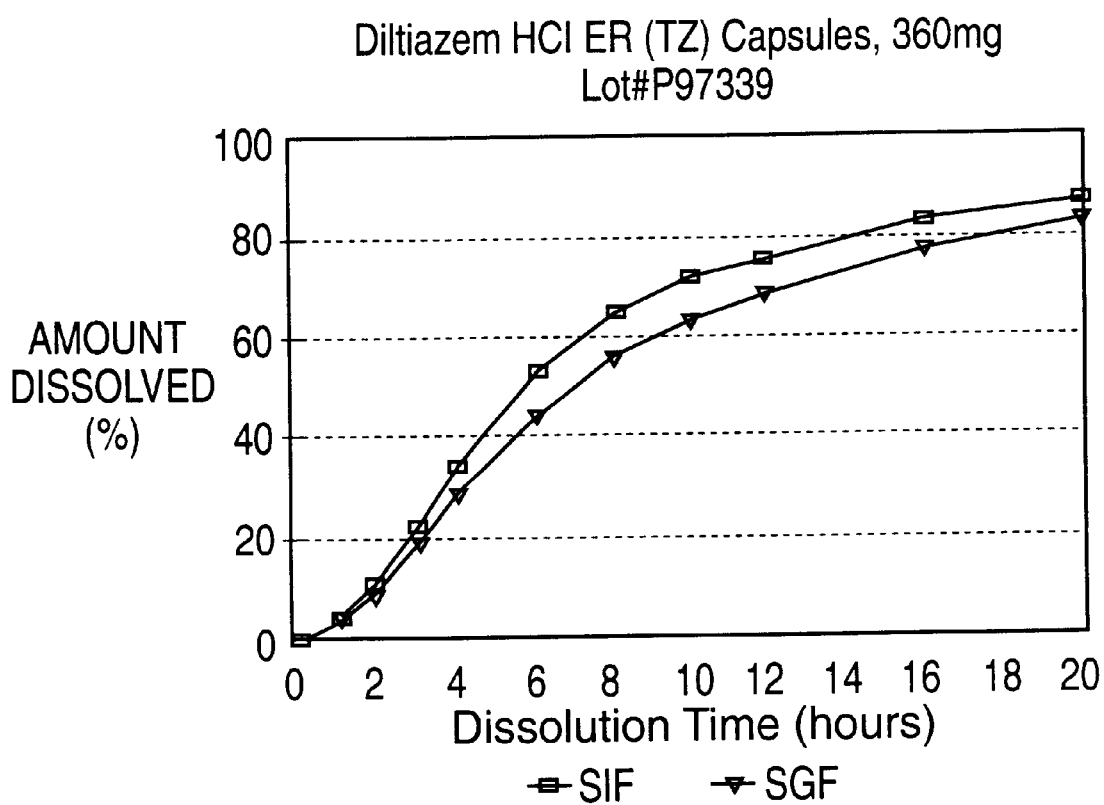
FIG. 4 is a graph depicting the dissolution profile in simulated intestinal fluid (pH 7.5 phosphate buffer) and simulated gastric fluid (SGF) of the formulation described in Example 2 as tested according to the procedure described in United States Pharmacopeia XXIII, Apparatus 2 @ 75 rpm.

The release profile in SIF (pH 7.5) and SGF of the controlled release product prepared in this Example is shown in FIG. 4.

Figure 7:
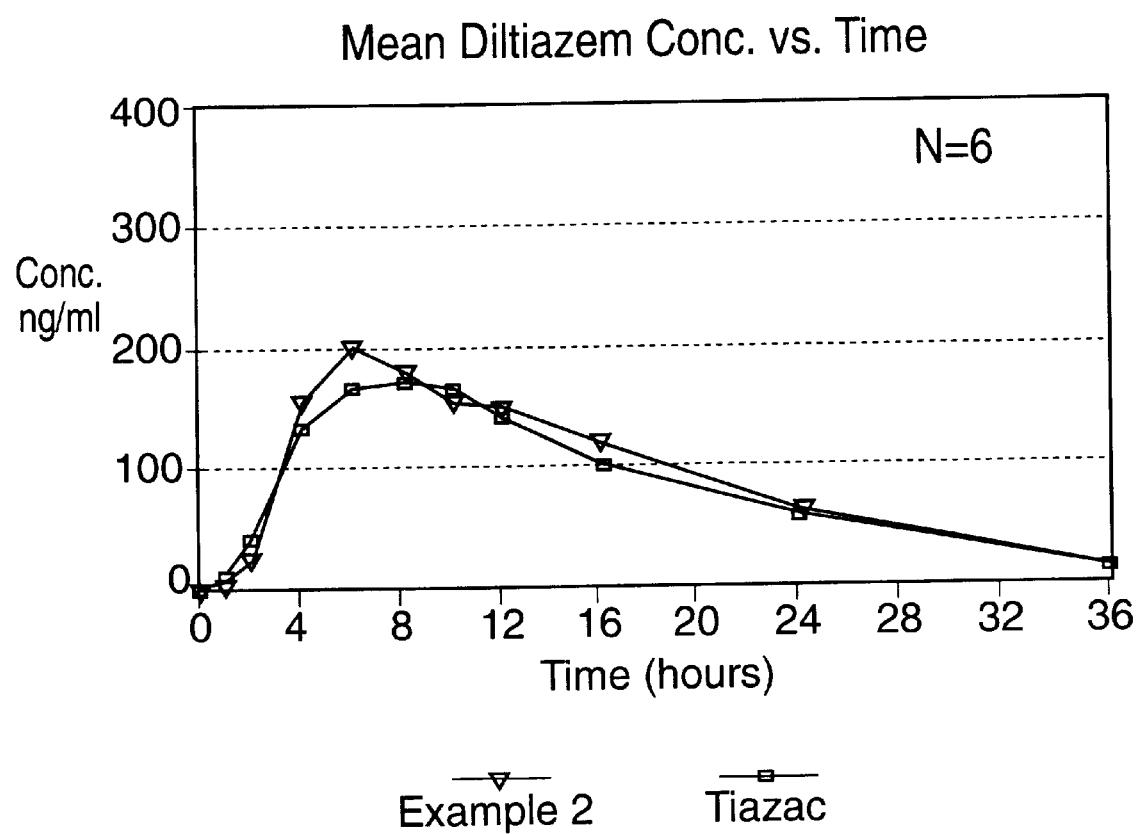
FIG. 7 is a graph depicting the in vivo diltiazem plasma profile of the formulation described in Example 2 and the in vivo diltiazem plasma profile of the commercially available diltiazem product TIAZAC™ under fasting conditions.

FIG. 7 depicts the in vivo diltiazem plasma profile of the controlled release product prepared in this Example. Also shown in FIG. 7 is the in vivo diltiazem plasma profile of TIAZAC™, a commercially available pharmaceutical product containing the drug diltiazem HCl.

Table 3 is a summary of the bioavailability comparison data under fasting conditions, test/reference ratio, shown in FIG. 7 wherein the TIAZAC™ product is the reference product in a two way crossover biostudy with n=6.

TABLE 3

|  | Test Mean | Ref Mean | G-Mean Ratio |
|---|---|---|---|
| $C_{max}$(ng/ml) | 201.67 | 187.33 | 1.087 |
| $AUC_{inf}$(ng · hr/ml) | 3566.34 | 3330.13 | 1.070 |

Figure 8:
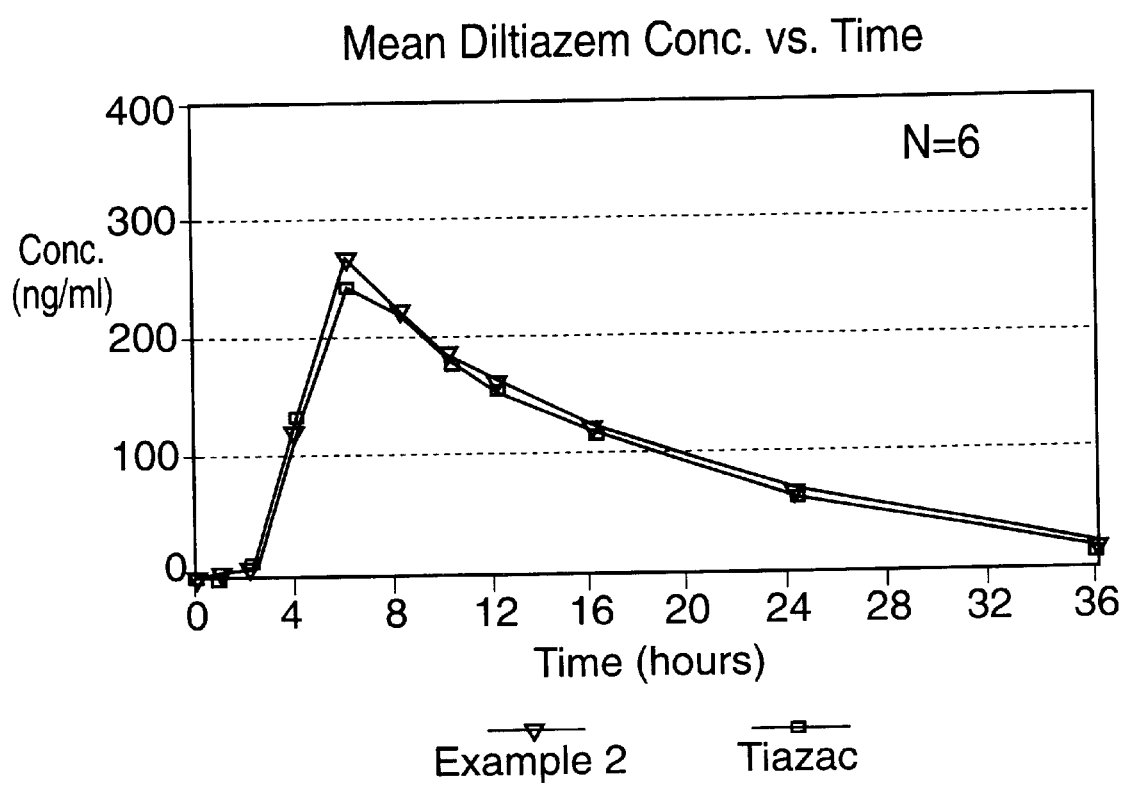
FIG. 8 is a graph depicting the in vivo diltiazem plasma profile of the formulation described in Example 2 and the in vivo diltiazem plasma profile of the commercially available diltiazem product TIAZAC™ under fed conditions.

FIG. 8 depicts the in vivo diltiazem plasma profile of the controlled release product prepared in this Example under fed conditions. FIG. 8 also shows the in vivo diltiazem plasma profile of the TIAZAC™ product under fed conditions.

Table 4 is a summary of the bioavailability comparison data under fed conditions, test/reference ratio, shown in FIG. 8 wherein the TIAZAC™ product is the reference product in a two way crossover biostudy with n=6.

TABLE 4

|  | Test Mean | Ref Mean | G-Mean Ratio |
|---|---|---|---|
| $C_{max}$(ng/ml) | 268.50 | 251.67 | 1.001 |
| $AUC_{inf}$(ng · hr/ml) | 3974.64 | 3826.76 | 1.019 |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A process for manufacturing a controlled release diltiazem dosage formulation comprising the steps of:
   a) adding a first allotment of active pellets containing diltiazem to a coating equipment;
   b) coating the first allotment of active pellets with a first amount of extended release coating;
   c) adding a second allotment of active pellets containing diltiazem to the equipment;
   d) coating the first and second allotment of active pellets with a second amount of extended release coating;
   e) optionally adding a third allotment of active pellets containing diltiazem to the equipment; and
   f) optionally coating the first, second and third allotments of active pellets with an optional third amount of extended release coating.

2. The process as defined in claim 1 wherein the weight of the first allotment of active pellets comprise 34–90% of the total weight of the active pellets to be coated, the weight of the second allotment of active pellets comprise 5–33% of the total weight of active pellets to be coated and the weight of the third allotment of active pellets is not optional and comprises 5–43% of the total weight of the active pellets to be coated, where the combined weight of the three allotments is 100%.

3. The process as defined in claim 2 wherein the weight of the first allotment of active pellets comprise 65–80% of the total weight of the active pellets to be coated, the weight of the second allotment of active pellets comprise 5–15% of the total weight of the active pellets to be coated and the weight of the third allotment of active pellets comprises 15–25% of the total weight of the active pellets to be coated, where the combined weight of the three allotments is 100%.

4. The process as defined in claim 1 wherein the weight of the first amount of extended release coating comprises 10–33% of the total amount of extended release coating to be applied to all active pellets, the weight of the second amount of extended release coating comprises 34–80% of the total amount of extended release coating to be applied to all the active pellets and the weight of the third amount of extended release coating is not optional and comprises 10–40% of the total amount of extended release coating to be applied to all the active pellets, where the combined weight of the extended release coating is 100%.

5. The process as defined in claim 4 wherein the weight of the first amount of extended release coating comprises 15–25% of the total amount of extended release coating to be applied to all the active pellets, the weight of the second amount of extended release coating to be applied to all the active pellets comprises 50–75% of the total amount of extended release coating to be applied to all the active pellets and the weight of the third amount of extended release coating comprises 15–30% of the total amount of extended release coating to be applied to all the active pellets, where the combined weight of the extended release coating is 100%.

6. A process for manufacturing a controlled release diltiazem dosage formulation comprising the steps of:
   a) adding a first allotment of active pellets which consist essentially of:
      (i) from 10–30% of a pharmaceutically acceptable inert core based on the total weight of the active pellets;
      (ii) from 50–85% of diltiazem or a pharmaceutically acceptable salt thereof based on the total weight of the active pellets;
      (iii) from 0.25–5% of a water soluble binder based on the total weight of the active pellets; and
      (iv) from 0.75–10% of a water insoluble binder based on the total weight of the active pellets;
   to a fluidized bed coating equipment wherein the active pellets are prepared by applying a suspension of the diltiazem, water soluble binder and the water insoluble binder to the inert core;
   b) coating the first allotment of active pellets with a first amount of extended release coating suspension which consists essentially of:
      (i) from 60–85% of a water insoluble water permeable polymer based on the total weight of the extended release coating;
      (ii) from 0.5–5% of a channeling agent based on the total weight of the extended release coating;
      (iii) from 5–20% of talc based on the total weight of the coating;
      (iv) 5–20% of magnesium stearate based on the total weight of the coating; and
      (v) 0 to less than 1% of a surfactant based on the total weight of the coating;
   c) adding a second allotment of active pellets as defined in step (a) to the equipment;
   d) coating the first and second allotment of active pellets with a second amount of extended release coating suspension as defined in step (b);
   e) adding a third allotment of active pellets as defined in step (a) to the equipment; and
   f) coating the first, second and third allotments of active pellets with a third amount of extended release coating suspension as defined in step (b) wherein the first allotment of active pellets comprise 34–90% of the total weight of active pellets to be coated, the second allotment of active pellets comprise 5–33% of the total weight of the active pellets to be coated and the third allotment of active pellets comprises 5–43% of the total weight of the active pellets to be coated and the first amount of extended release coating suspension comprises 10–30% of the total amount of extended release coating suspension to be applied to all the active pellets, the second amount of extended release coating suspension comprises 34–80% of the total amount of extended release coating suspension to be applied to all the active pellets and the third amount of extended release coating suspension comprises 10–40% of the total amount of extended release coating suspension to be applied to all the active pellets.

7. The process as defined in claim 6 wherein the first allotment of active pellets comprise 65–80% of the total weight of active pellets to be coated, the second allotment of active pellets comprise 5–15% of the total weight of the active pellets to be coated and the third allotment of active pellets comprises 15–25% of the total weight of the active pellets to be coated and the first amount of extended release coating comprises 15–25% of the total amount of extended release coating to be applied to all the active pellets, the second amount of extended release coating comprises 50–75% of the total amount of extended release coating to be applied to all the active pellets and the third amount of extended release coating comprises 15–30% of the total amount of extended release coating to be applied to all the active pellets.

8. A product prepared according to the process defined in claim 6 that exhibits the following dissolution profile when tested in a United States Pharmacopoeia type 2 apparatus at 100 rpm in 900 ml of 0.1 N HCL and at 37° C.:
   after 2 hours 0–30% of the diltiazem is released;
   after 4 hours 5–45% of the diltiazem is released;
   after 8 hours 20–70% of the diltiazem is released;
   not less than 45% of the diltiazem is released after 12 hours;
   not less than 55% of the diltiazem is released after 18 hours;
   and not less than 65% of the diltiazem is released after 20 hours.

9. The product as defined in claim 8 that exhibits the following dissolution profile when tested in a United States Pharmacopoeia type 2 apparatus at 100 rpm in 900 ml of 0.1 N HCL and at 37° C.:
   after 2 hours 5–25% of the diltiazem is released;
   after 4 hours 10–35% of the diltiazem is released;
   after 8 hours 35–65% of the diltiazem is released;
   not less than 50% of the diltiazem is released after 12 hours;
   not less than 60% of the diltiazem is released after 18 hours;
   and not less than 70% of the diltiazem is released after 20 hours.

10. The process as defined in claim 6 wherein the diltiazem or a pharmaceutically acceptable salt is micronized.

11. The process as defined in claim 6 wherein the binder employed in the active pellets is selected from the group consisting of polyvinyl pyrrolidone, hydroxyethylcellulose, hydroxypropyl cellulose, hydroxypropyl methylcellulose, polyacrylate and ethylcellulose or a mixture thereof.

12. The process as defined in claim 6 wherein the binder employed in the active pellet is a combination of a water soluble binder and a water insoluble binder.

13. The process as defined in claim 12 wherein the ratio of water soluble binder to water insoluble binder is about 1:1 to about 1:3.

14. The process as defined in claim 13 wherein the ratio of water soluble binder to water insoluble binder is about 1:2.

15. The process as defined in claim 12 wherein the water soluble binder is polyvinyl pyrrolidone and a water insoluble binder is ethylcellulose.

16. The process as defined in claim 12 wherein the water soluble binder comprises about 0.25–5% of the total weight of the active pellet and the water insoluble binder comprises about 0.75–10% of the total weight of the active pellet.

17. The process as defined in claim 6 wherein the water insoluble water permeable polymer of the extended release coating is selected from the group consisting of ethylcellulose, cellulose acetate, polyacrylates or mixtures thereof.

18. The process as defined in claim 17, wherein the water insoluble water permeable polymer is a poly(ethylacrylate methylmethacrylate) copolymer.

19. The process as defined in claim 6 wherein the channeling agent employed in the extended release coating is a water or acid soluble pharmaceutically acceptable substance selected from the group consisting of polyvinyl pyrolidone, hydroxyethylcellulose, hydroxypropyl cellulose, hydroxypropyl methycellulose, polyacrylate, sucrose, diltiazem, a pharmaceutically acceptable salt of diltiazem and any combination of the foregoing.

20. The process as defined in claim 19 wherein the channeling agent is hydroxypropyl methylcellulose.

21. The process as defined in claim 6 wherein the lubricant is selected from the group consisting of talc, magnesium stearate, silicon dioxide, kaolin and a mixture of the foregoing.

22. The process as defined in claim 21 wherein the lubricant is a mixture of talc and magnesium stearate.

23. The process as defined in claim 22 wherein the ratio of talc to magnesium stearate is about 1:2 to about 2:1.

24. The process as defined in claim 6 wherein the surfactant is polysorbate 80.

25. The process as defined in claim 8 wherein the inert core is a non-pareil seed of sugar or starch having a diameter ranging from about 15–50 mesh.

26. The process as defined in claim 6 wherein the first, second, and third allotment of active pellets are coated with varying number of layers of extended release coating wherein said extended release coating consists of a homogeneous mixture comprising about 60–85% of poly (ethyl acrylate methylacrylate) copolymer and a channeling agent.

* * * * *